CHRYSANTHEMUM PLANT
Filed July 30, 1974
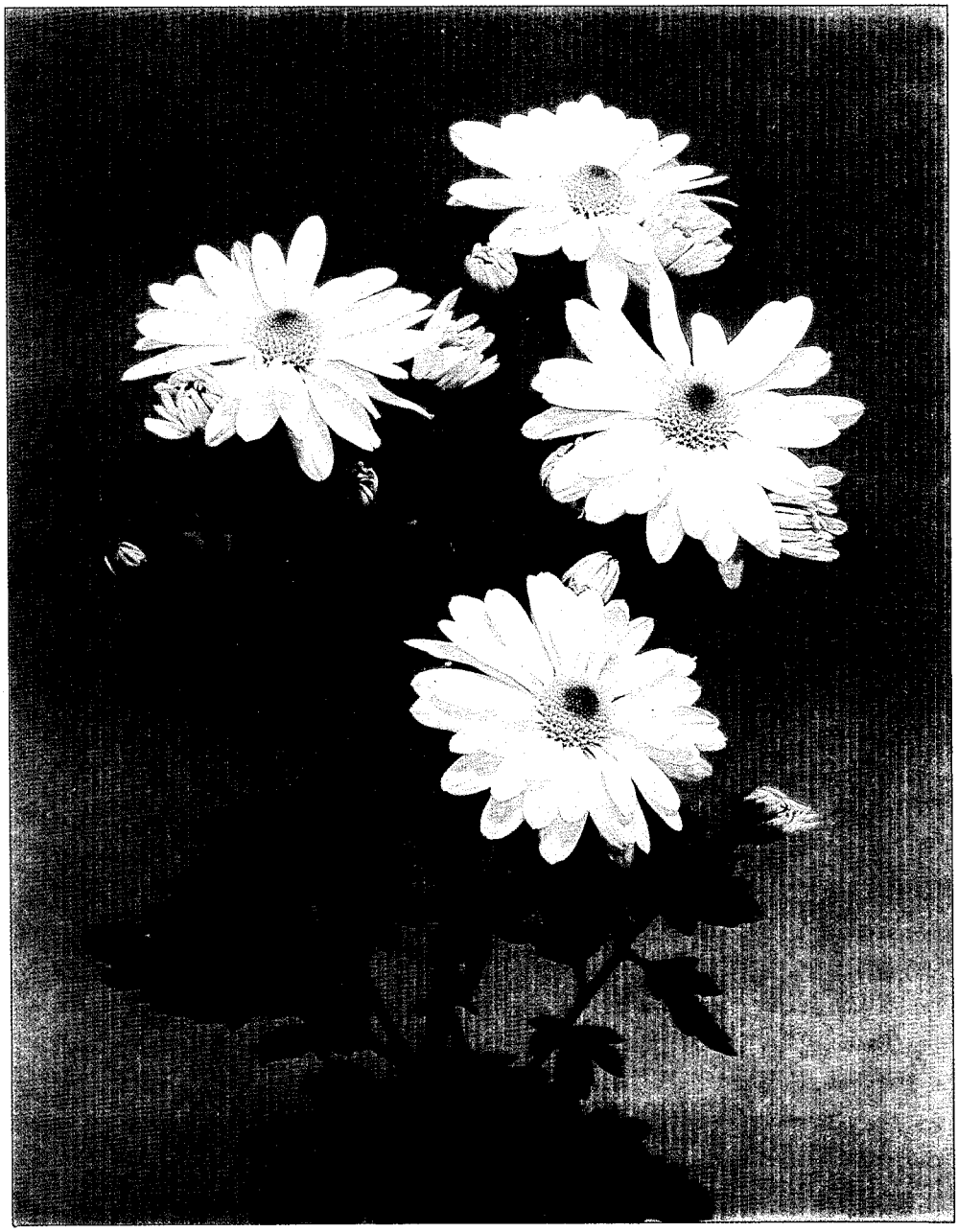

United States Patent Office

Plant Pat. 3,778
Patented Sept. 2, 1975

3,778
CHRYSANTHEMUM PLANT

Walter H. Jessel, Jr., Doylestown, and William H. Duffett, Akron, Ohio, assignors to Yoder Brothers, Inc., Barberton, Ohio

Filed July 30, 1974, Ser. No. 493,048
Int. Cl. A01h *5/00*
U.S. Cl. Plt.—74 1 Claim

The present invention comprises a new and distinct cultivar of chrysanthemum plant known by the varietal name Celebration which is a seeding of #67–100–005 × #67079–001, the breeding number of the cultivar Dramatic, disclosed in U.S. Plant Pat. No. 3,189. The unpatented parent is identified for breeding purposes by the indicated breeding number.

The new cultivar is similar in many respects to the cultivar Florida Marble, disclosed in U.S. Plant Pat. 3,288, the new cultivar having the same characteristics as Florida Marble of:

1. Use as a yellow daisy for controlled flowering programs April 15 through November 15.
2. Vigor and general growth characteristics.
3. Tolerance of marginal temperatures for uniform bud initiation and development down to 54° F.

The new cultivar is distinguished from Florida Marble by the following characteristics when grown under comparable conditions:

1. A more intense golden yellow flower color, and longer color retention.
2. A more duplex daisy form.
3. Improved tolerance of high temperatures with minimum compounding and resultant delay in response.
4. No known foliar problems.
5. More rapid aging of center disc.
6. No bracting or petaloid development of disc florets under high and low temperatures during bud development.
7. Three to four more flowers per terminal spray.
8. Improved color retention.

9. Foliage which is somewhat shorter in length but greater in width.

The new cultivar was selected from the progeny of the designated cross, and when asexually reproduced by cuttings at Barberton, Ohio, has been found to retain its distinctive characteristics through successive propagation.

The new cultivar, when grown in the vicinity of Barberton, Ohio, has a response time of approximately 8 weeks, and has an approximate response period as follows:

Late 7 week—April 15 through May 15, and November 1 through November 15.
Early-to-mid 8 week—May 15 through November 1.

The following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern United States is from April 15 through November 15; southeastern United States and southwestern United States, April through November; costal California, year round, and southern Florida under outdoor conditions, November through April.

The accompanying color photographic drawing shows the unique characteristics of our new cultivar, the color being as nearly true as possible with color illustrations of this type.

In the following description, color references are made to the Munsell Limit Color Cascade, 1972 edition (designated MLCC), and Munsell Book of Color, 1963 edition (designated MBC). Comparisons are made with the cultivar Florida Marble. Where only a single value or description appears for the new cultivar the same value or description applies as well to the comparison cultivar Florida Marble.

Botanical classification: *Chrysanthemum morifolium*, Ramat.

| | Celebration | Florida Marble |
|---|---|---|
| Bloom: | | |
| Size | 2¾″ to 3¼″ | 2¾″. |
| Fully expanded | 3½″ | 3¼″. |
| Borne | In clusters on terminal sprays | In clusters on compound sprays. |
| Stems | Strong | Strong. |
| Form | Daisy (duplex) | Daisy (single). |
| Permanence | 10–12 days | 7 days. |
| Color: | | |
| Center of flower | Medium green, 5.4GY6.0/11.0 (MLCC) to yellow, 7.5Y8/10 (MBC). | Light green, 2.5GY5/8 to dark yellow, 6.25Y8.5/12 (MBC). |
| Base of petals | Medium green, 5.4GY6.9/12.6 (MLCC) | Yellow, 7.5Y8.5/10 (MBC). |
| Inside of petals | Dark yellow, 8.2Y8.7/14.7 (MLCC) | Yellow, 7.5Y8.5/10 to light yellow 7.5Y9/6 (MBC). |
| Reverse of petals | Yellow, 7.5Y8.8/7.2 (MLCC) | Yellow, 7.5Y8.5/8 to light yellow, 7.5Y9/6 (MBC). |
| Tonality from a distance | Golden yellow | Clear yellow. |
| Discoloration | Yellow, 7.4Y8.7/9.6 (MLCC) | Light yellow, 7.5Y9/6 (MBC). |
| Petals: | | |
| Texture | Smooth | |
| Appearance and form | Closed at base, flaring quickly to a flat ridged keel, tapering to a blunt 2-notched tip with occasional reverse roll along petal margins. | Open at base, broad flat keel, tapering to a rounder tip. |
| Arrangement | Composite, whorled on a single receptacle | |
| Persistence | Resists shatter | |
| Fragrance | Typical chrysanthemum | |
| Reproductive organs: | | |
| Stamen, anthers | 250+ | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Upright | |
| Height | Approximately 44″–49″ given 2–3 long day weeks, and total crop time of 10 weeks as defined in the timetables of Yoder Brothers, Inc., Barberton, Ohio, for the various seasons. | Approximately 44″–49″ given 2–3 long day weeks, and total crop time of 10–12 weeks as defined in the timetables of Yoder Brothers, Inc., Barberton, Ohio, for the various seasons. |
| Spread | None grown single stem to slight grown pinched | |

| | Celebration | Florida Marble |
|---|---|---|
| Foliage: | | |
| Top side | Dark green, 5.6GY2.3/3.6 (MLCC) | Dark green, 7.5GY3/4 (MBC). |
| Size | Length to width ratio 10:7 with length up to 5″ and width to 3½″. | Length to width ratio 24:13 with length to 6″ and width to 3¼″. |
| Quantity | Numerous | |
| Shape | Spatulate lobed | |
| Texture | Smooth | |
| Ribs and veins | Prominent | |
| Edge | Deeply indented | Moderately indented. |
| Serration | Coarse | Moderate. |
| Under side | Greyed green, 7.5GY5/4 (MBC) | |
| Stipules | Very prominent | Prominent. |

We claim:

1. A new and distinct cultivar of chrysanthemum characterized particularly as to its uniqueness when compared to the cultivar Florida Marble by its more intense golden yellow flower color, and longer color retention; more duplex daisy form; improved tolerance of high temperatures with minimum compounding and resultant delay in response; no known foliar problems; more rapid aging of center disc; no bracting or petaloid development of disc florets under high and low temperatures during bud development; three to four more flowers per terminal spray, and by its improved color retention.

No references cited.

ROBERT E. BAGWILL, Primary Examiner